(12) United States Patent
Bromba

(10) Patent No.: US 6,676,611 B1
(45) Date of Patent: Jan. 13, 2004

(54) DEVICE AND METHOD FOR EXTRACTING PHYSIOLOGICAL DATA

(75) Inventor: Manfred Bromba, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/009,107

(22) PCT Filed: Apr. 26, 2000

(86) PCT No.: PCT/DE00/01292
§ 371 (c)(1),
(2), (4) Date: Dec. 3, 2001

(87) PCT Pub. No.: WO00/74566
PCT Pub. Date: Dec. 14, 2000

(30) Foreign Application Priority Data

Jun. 2, 1999 (DE) .......................... 199 25 410

(51) Int. Cl.⁷ .......................... A61B 5/117; A61B 5/103
(52) U.S. Cl. ........................ 600/587; 600/306
(58) Field of Search ................. 600/300, 306, 600/372, 382, 384, 587; 382/115, 124, 125

(56) References Cited

U.S. PATENT DOCUMENTS

| 5,635,723 A | * | 6/1997 | Fujieda et al. | 250/556 |
| 5,828,773 A | * | 10/1998 | Setlak et al. | 382/126 |
| 6,131,464 A | * | 10/2000 | Pare et al. | 73/714 |
| 6,327,376 B1 | * | 12/2001 | Harkin | 382/124 |

FOREIGN PATENT DOCUMENTS

| DE | 40 26 167 A1 | 5/1991 |
| FR | 2 406 986 | 5/1979 |
| FR | 2 674 051 | 9/1992 |
| FR | 2 736 179 | 1/1997 |
| JP | 10 290796 | 11/1998 |
| WO | WO 98/18385 | 5/1998 |

OTHER PUBLICATIONS

Physicochemical techniques in the development of latent fingerprints, Pounds et al.

* cited by examiner

Primary Examiner—Charles Marmor
(74) Attorney, Agent, or Firm—Bell Boyd & Lloyd LLC

(57) ABSTRACT

An apparatus and a method for extracting physiological data from the skin of a body, wherein the apparatus includes at least one fingerprint sensor for ascertaining a blackening profile and a pressure sensor for measuring a pressure profile for a pressure exerted on the fingerprint sensor.

6 Claims, 1 Drawing Sheet

DEVICE AND METHOD FOR EXTRACTING PHYSIOLOGICAL DATA

BACKGROUND OF THE INVENTION

The present invention relates to an apparatus and to a method for noninvasively extracting physiological data from the skin of the body.

Noninvasive extraction of physiological data from the skin of the body is used either for medical purposes or for lie detection. By way of example, during a court hearing, a security check or a job interview, great importance is attached to the person to be examined; e.g., a witness or a defendant, telling the truth.

Methods for noninvasively extracting physiological data from the skin are known in which production of body perspiration is ascertained via measurement of the resistance of the skin, for example by electrodes attached to the upper body.

Lie detection is based, among other things, on the observation that deliberate lying results in a physical reaction of the skin.

It is an object of the present invention to provide a way of noninvasively extracting physiological data from the skin of the body which is easy to apply.

SUMMARY OF THE INVENTION

The apparatus of the present invention is designed such that it has at least one fingerprint sensor for ascertaining production of perspiration.

In this context, the fingerprint sensor is used to record a degree of blackening, and a change in the degree of blackening is used to measure a change in production of perspiration by the finger which has been placed on the fingerprint sensor. A change in the blackening image over time provides a blackening profile.

In this case, the degree of blackening corresponds essentially to the finger's contact area detected by the fingerprint sensor. In the event of increased perspiration production, the blackening image recorded by the fingerprint sensor also becomes darker, on average. The reason for this is, among other things, that the greater presence of body perspiration on the finger increases the pressure transferred from the finger to the fingerprint sensor, and that a larger area of the fingerprint sensor is occupied.

This method of noninvasively extracting physiological data has the advantage that it is possible to ascertain evidence relating to the production of body perspiration by simply applying a finger.

It is thus possible to dispense with any further attachment of apparatuses to the human body, for example, sleeves for measuring the pulse or adhesive strips for ascertaining the resistance of the skin. As such, it is also possible to provide a compact and portable apparatus for noninvasively extracting physiological data.

The apparatus may also have more than one fingerprint sensor; for example, two fingerprint sensors for two different fingers of a hand or on both hands. The apparatus also may be equipped with fingerprint sensors for each finger.

While the apparatus is operating, the pressure exerted on the fingerprint sensor by the finger may vary. However, any variation in the contact pressure results in a change in the blackening image due to the changing contact area. It is, therefore, desirable to separate the influence of the pressure from the influence of perspiration production on the blackening profile.

On the basis of this, it is advantageous for the lie detector to be equipped not only with the at least one fingerprint sensor but also with at least one pressure sensor which is able to measure the pressure exerted on the fingerprint sensor by the finger.

In this regard, the pressure sensor is expediently mounted on the side which is remote from the fingerprint sensor's surface provided for applying the finger. A finger, therefore, presses on the fingerprint sensor, which, in turn, presses on the pressure sensor.

This makes it possible to record the blackening profile from the fingerprint sensor and the pressure profile from the pressure sensor at the same time and to subject the degree of blackening to pressure-normalization; i.e., to ascertain it largely independently of the pressure by adjusting the blackening profile with the pressure profile.

It is also advantageous for the pressure-normalized or non-pressure-normalized blackening profile to be examined for cyclic components. The cyclic components can be used to ascertain the pulse or, when plotted against time, the pulse profile. To this end, there is advantageously an evaluation circuit for ascertaining cyclic components of the blackening profile.

This method of noninvasively extracting physiological data can be used advantageously for lie detection.

Taking into account the time of a statement, the blackening profile can be used to draw conclusions about a truth content of the statement. By way of example, one indication of a lie may be if, upon hearing a question or when responding to a question, there is significantly greater production of perspiration, in line with a local maximum in the advantageously pressure-normalized blackening profile.

Additionally using the pulse profile provides another way of ascertaining a physical reaction during lie detection. This is because hearing a question or responding to a question may also produce a higher pulse rate, for example.

The method of noninvasively extracting physiological data can also be used for detecting life. In this context, it is assumed that detection of a pulse profile refers to a finger applied to the apparatus being attached to a living person.

Detection of life can be used in identification machines based on fingerprint profiles; e.g., on cash machines or on security safeguards. Using detection of life makes it possible to establish whether the finger placed on the identification machine is still attached to a blood circulation or whether it has been removed from an authorized person in order to gain access by devious methods, for example.

This also can be used advantageously for detecting apparent death. To this end, the apparatus with pulse detection is strapped to a finger of a person regarded as dead, for example. If the apparatus detects a pulse, an alarm is triggered. For this purpose, the apparatus is preferably lightweight and portable and is equipped with a transmitter. Preferably, the radio waves emitted by the transmitter also should be able to penetrate a layer of earth, typically having a thickness of between half a meter and two meters.

Additional features and advantages of the present invention are described in, and will be apparent from, the following Detailed Description of the Invention and the Figures.

DETAILED DESCRIPTION OF THE INVENTION

Figure 1:
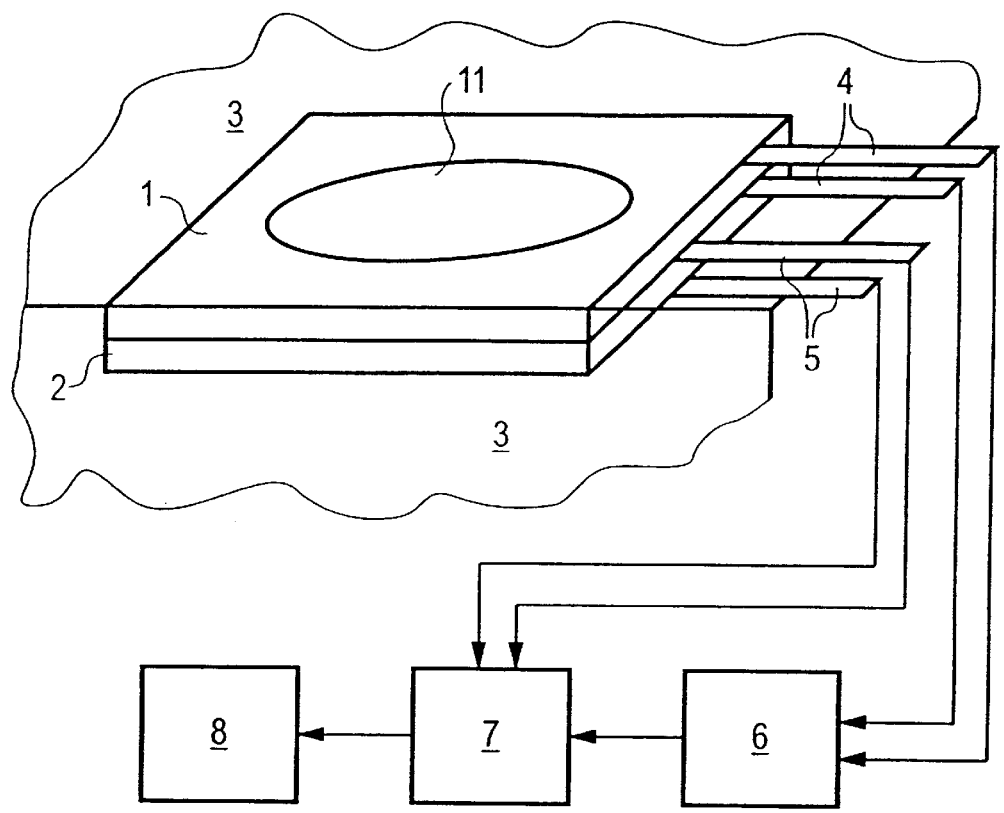
FIG. 1 shows a schematic oblique view of an exemplary embodiment of inventive apparatus.

FIG. 1 describes a lie detector. A housing 3 contains a fingerprint sensor 1 which is connected via electrical connections 4 to a perspiration evaluation unit 6 for ascertaining a degree of blackening or a blackening profile. That side of the fingerprint sensor 1 which is remote from the contact area 11 of a finger has a pressure sensor 2 mounted on it which takes an at least proportional measurement of a pressure applied to the fingerprint sensor 1.

The pressure sensor 2 is connected via electrical connections 5 to a normalization unit 7. The blackening profile and the pressure profile are put into the normalization unit 7, in which a pressure-normalized blackening profile is ascertained. The pressure-normalized blackening profile is used to ascertain the pulse on the finger in a pulse unit 8 for determining cyclic components.

During a lie detector test, the test person presses his/her finger onto the contact area 11 of the fingerprint sensor 1. The test person is then asked questions, and the blackening profile is recorded at the same time. By correlating the normalized blackening profile and the test questions and/or the pulse ascertained in the pulse unit 8, it is possible to draw conclusions about the truth content of the test person's responses to the questions asked.

Although the present invention has been described with reference to specific embodiments, those of skill in the art will recognize that changes may be made thereto without departing from the spirit and scope of the invention as set forth in the hereafter appended claims.

What is claimed is:

1. An apparatus for extracting physiological data from skin of a body, comprising:

at least one fingerprint sensor for detecting a blackening density profile, the at least one fingerprint sensor having a contact surface;

a pressure sensor via which a pressure profile of a pressure exerted on the contact surface of the at least one fingerprint sensor can be measured, the pressure sensor being disposed at the at least one fingerprint sensor on a side opposite that of the contact surface; and a normalization unit to which the blackening density profile and the pressure profile are fed for purposes of generating a pressure-normalized blackening density profile.

2. An apparatus for extracting physiological data as claimed in claim 1, further comprising a pulse unit to which the pressure-normalization blackening density profile is fed for purposes of detecting periodic portions of the pressure-normalized blackening density profile.

3. An apparatus for extracting physiological data as claimed in claim 1, wherein the apparatus is incorporated into a lie detector.

4. An apparatus for extracting physiological data as claimed in claim 1, wherein the apparatus is incorporated into a life detection instrument.

5. A method for lie detection using a lie detector which includes an apparatus for extracting physiological data from skin of a body, the method comprising the steps of:

providing, as part of the apparatus, at least one fingerprint sensor for detecting a blackening density profile, the at least one fingerprint sensor having a contact surface;

providing, as part of the apparatus, a pressure sensor via which a pressure profile of a pressure exerted on the contact surface of the at least one fingerprint sensor can be measured, the pressure sensor being disposed at the at least one fingerprint sensor on a side opposite to the contact surface; and correlating a variation in the blackening density profile to at least one question asked of a test person and at least one response given by the test person.

6. A method for detecting life using an apparatus for extracting physiological data from skin of a body, the method comprising the steps of:

providing, as part of the apparatus, at least one fingerprint sensor for detecting a blackening density profile, the at least one fingerprint sensor having a contact surface;

providing, as part of the apparatus, a pressure sensor via which a pressure profile of a pressure exerted on the contact surface of the at least one fingerprint sensor can be measured, the pressure sensor being disposed at the at least one fingerprint sensor on a side opposite to the contact surface;

providing, as part of the apparatus, a pulse unit for ascertaining cyclic components of the blackening density profile; and providing an alarm signal upon detection of the cyclic components.

* * * * *